United States Patent
Vestal et al.

(10) Patent No.: US 10,359,440 B2
(45) Date of Patent: Jul. 23, 2019

(54) MASS SPECTROMETRY METHOD AND APPARATUS FOR CLINICAL DIAGNOSTIC APPLICATIONS

(71) Applicant: Virgin Instruments Corporation, Marlborough, MA (US)

(72) Inventors: Marvin L. Vestal, Framingham, MA (US); Kevin Hayden, Newton, MA (US)

(73) Assignee: Virgin Instruments Corporation, Marlborough, MA (US)

(*) Notice: Subject to any disclaimer, the term of this patent is extended or adjusted under 35 U.S.C. 154(b) by 454 days.

(21) Appl. No.: 15/080,131

(22) Filed: Mar. 24, 2016

(65) Prior Publication Data

US 2016/0291047 A1    Oct. 6, 2016

Related U.S. Application Data

(60) Provisional application No. 62/139,889, filed on Mar. 30, 2015.

(51) Int. Cl.
*H01J 49/00* (2006.01)
*G01N 35/00* (2006.01)
(Continued)

(52) U.S. Cl.
CPC . *G01N 35/00871* (2013.01); *G01N 35/00029* (2013.01); *G01N 35/0099* (2013.01);
(Continued)

(58) Field of Classification Search
CPC .............. H01J 49/0413; H01J 49/0418; G01N 35/0099; B01L 3/50273; B01L 3/502753; B01L 3/502715; B01L 3/502784
See application file for complete search history.

(56) References Cited

U.S. PATENT DOCUMENTS

| 2004/0021071 A1* | 2/2004 | Mordekhay ......... H01J 49/0413 |
| | | 250/288 |
| 2005/0173627 A1 | 8/2005 | Cotter et al. |

(Continued)

OTHER PUBLICATIONS

"Notification of Transmittal of the International Search Report and the Written Opinion of the International Searching Authority, or the Declaration" for PCT/US2016/024045, dated Jul. 20, 2016, 15 pages, ISA/KR, Korean Intellectual Property Office, Daejeon, Republic of Korea.

(Continued)

*Primary Examiner* — Wyatt A Stoffa
*Assistant Examiner* — Hsien C Tsai
(74) *Attorney, Agent, or Firm* — Kurt Rauschenbach; Rauschenbach Patent Law Group, LLC

(57) ABSTRACT

A mass spectrometer system for analysis of clinical samples includes a source of clinical samples. A controller receives the clinical samples from the source of clinical samples. A sample preparation system receives clinical sample from the controller and processes the samples to produce an extract suitable for analysis by MALDI-TOF mass spectrometry and deposits the extract on a sample plate together with a MALDI matrix. A sample plate loading mechanism transports sample plates from the sample preparation system into an evacuated ion source of a MALDI-TOF mass spectrometer. A MALDI-TOF mass spectrometer ionizes and analyzes samples on the sample plate and generates a mass spectrum of components in the clinical samples. A computer system receives data from the MALDI-TOF mass spectrometer and processes and interprets the data to generate a mass spectrum.

26 Claims, 7 Drawing Sheets

(51) Int. Cl.
    H01J 49/16    (2006.01)
    H01J 49/40    (2006.01)
    H01J 49/04    (2006.01)
(52) U.S. Cl.
    CPC . *G01N 35/00584* (2013.01); *G01N 35/00732* (2013.01); *H01J 49/0027* (2013.01); *H01J 49/0413* (2013.01); *H01J 49/164* (2013.01); *H01J 49/40* (2013.01); *G01N 2035/00158* (2013.01); *G01N 2035/00752* (2013.01); *G01N 2035/00851* (2013.01)

(56) References Cited

U.S. PATENT DOCUMENTS

| | | |
|---|---|---|
| 2010/0213074 A1 | 8/2010 | Mousa et al. |
| 2012/0270206 A1* | 10/2012 | Ginns ................ C12Q 1/6876 435/5 |
| 2013/0320203 A1 | 12/2013 | Roder et al. |

OTHER PUBLICATIONS

Notification Concerning Transmittal of International Preliminary Report on Patentablity(Chapter I of the Patent Cooperation Treaty) for PCT/US2016/024045, dated Oct. 12, 2017, 12 pages, The International Bureau of WIPO, Geneva Switzerland.

* cited by examiner

MASS SPECTROMETRY METHOD AND APPARATUS FOR CLINICAL DIAGNOSTIC APPLICATIONS

CROSS REFERENCE TO RELATED APPLICATION

The present application is a non-provisional application of U.S. Provisional Patent Application No. 62/139,889, entitled "Mass Spectrometry Method and Apparatus for Clinical Diagnostic Applications" filed on Mar. 30, 2015. The entire contents of U.S. Provisional Patent Application No. 62/139,889 are herein incorporated by reference.

INTRODUCTION

Matrix assisted laser desorption/ionization time-of-fight mass (MALDI-TOF) spectrometry has become an established technique for analyzing a variety of nonvolatile molecules including proteins, peptides, oligonucleotides, lipids, glycans and other molecules of biological importance. While MALDI TOF spectrometry technology has been applied to many analytical applications, widespread acceptance for clinical applications has been limited by many factors, including, for example, the cost and complexity of these instruments, relatively poor reliability and insufficient performance, such as insufficient speed, sensitivity, resolution and mass accuracy. The present invention provides a method and apparatus for overcoming these and other limitations.

Different types of TOF analyzers are required for different analytical applications, depending on the properties of the molecules to be analyzed. For example, a simple linear analyzer is preferred for analyzing high mass ions, such as intact proteins, oligonucleotides and large glycans, while a reflecting analyzer is required to achieve sufficient resolving power and mass accuracy for analyzing peptides and small molecules. Determining the molecular structure by MS-MS techniques requires yet another analyzer. In some commercial instruments, all of these types of analyzers are combined in a single instrument. Such combined instruments have the advantage of reducing the cost somewhat relative to owning and operating three separate instruments. However, these combined instruments have the disadvantage of there being a substantial increase in instrument complexity, a reduction in reliability and other compromises, which make the performance of all of the analyzers less than optimal.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way.

DESCRIPTION OF VARIOUS EMBODIMENTS

Figure 1:
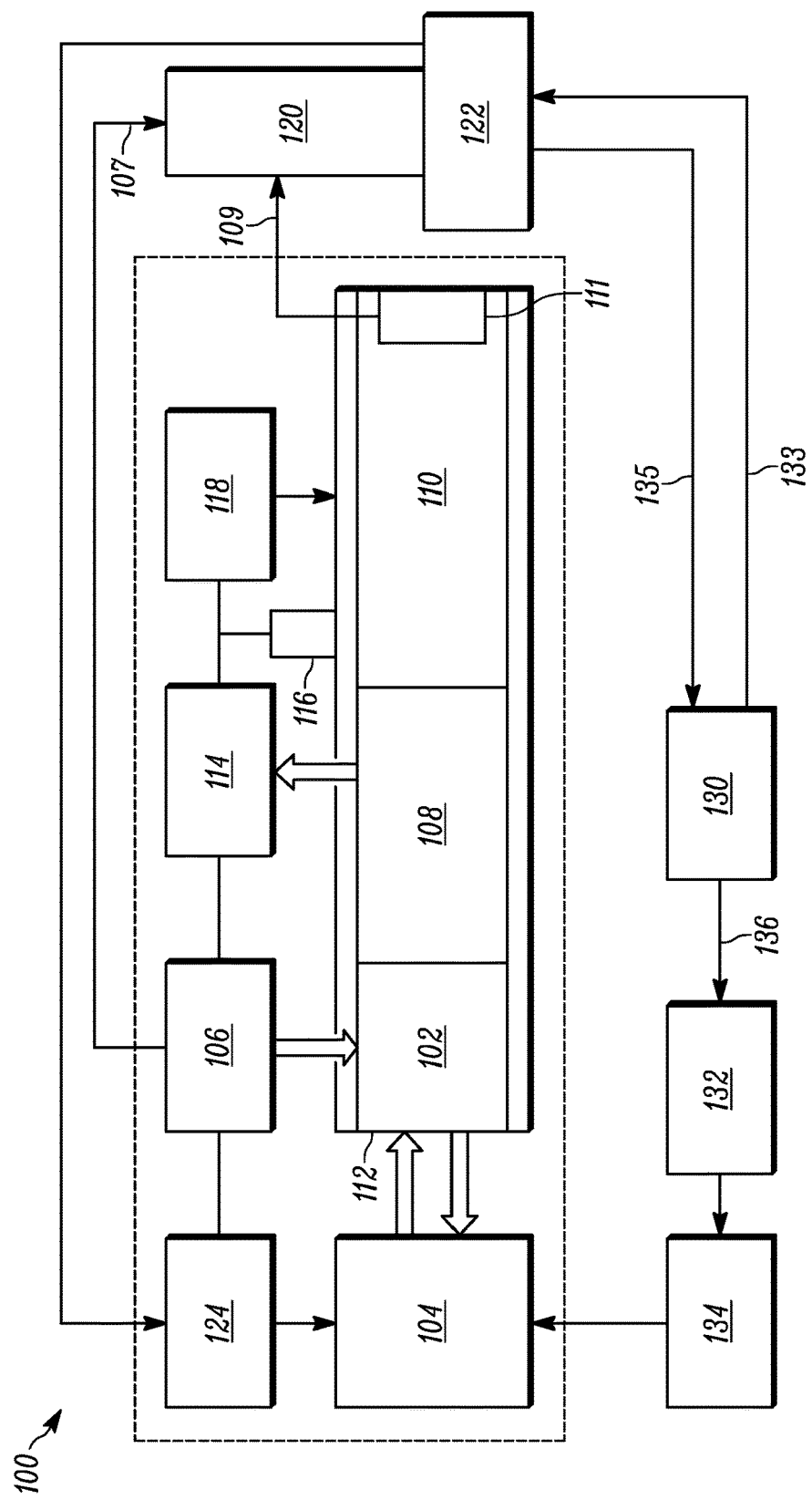
FIG. 1 illustrates a block diagram of an embodiment of a MALDI-TOF mass spectrometer system.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

One aspect of the present teaching is to provide a mass spectrometer method and apparatus that is suitable for performing routine analyses on selected analytes in a clinical or diagnostic laboratory. It is desired for such an instrument that it provide the needed accuracy, resolution, sensitivity and dynamic range to provide the basic information required to perform the selected assay with a specified performance. It may also be desirable that such an instrument be fully automated and require little or no training or experience on the part of the operator. In some embodiments, the system is self-contained in a single cabinet, except for an external computer, and must be small and light enough to fit comfortably on a standard laboratory bench in a clinical laboratory. The instrument must be compatible with either manual or automated sample preparation procedures that are routinely employed in a clinical or diagnostic laboratory, and results must be both presented in a form specified by the clinician submitting the samples and accessible from remote computers. In many embodiments, the speed of the analysis is not the limit on sample throughput. Additionally, the instrument must be simple, reliable and robust, requiring no tuning to obtain stable and predictable results.

Prior art MALDI-TOF mass spectrometers used laser pulse repetition rates that were often limited to about 50 Hz or less, and a small number of laser shots (typically 50-500) were summed to produce a spectrum. Prior art MALDI-TOF mass spectrometers acquired data by looking for "sweet spots" on the MALDI samples, and with samples deposited on a spot with a nominal diameter of ca. 3 mm, only a small fraction, which was typically less than 1% of the sample molecules, were ionized and then subsequently analyzed. In the MALDI-TOF instruments of the present teaching, the laser pulse repetition rate is in the range 1-5 kHz and the laser spot is rastered over the sample spot in order to ionize and analyze a large fraction of the sample on a sample spot. At least 10,000 laser shots are summed to obtain a spectrum, and as many as 200,000 laser shots can be employed, as necessary, to completely ionize a sample.

Mass spectrometer apparatus according to the present teaching provides a much simpler and less expensive means for transferring sample plates from atmospheric pressure to an evacuated chamber of a mass spectrometer. In particular, one feature of the method and apparatus of the present teaching is that sample plates can be manually loaded and unloaded. In one embodiment, there is a simplified vacuum system that requires no valves or conventional load lock chamber. One aspect of the sample plate handling of the present teaching is that, in some embodiments, gate valves isolating the mass spectrometer instrument are eliminated entirely. The gate valves in many known mass spectrometers are needed to seal the various chambers for separate pump down cycles. The gate valves used in known prior art mass spectrometers are generally complex and expensive and their use increases the processing time of the mass spectrometric analysis.

In some embodiments of the sample plate handling system of the present teaching present, new samples are introduced through a chamber with a volume that is much smaller than the volume of the analysis chamber. This reduces or eliminates the need for conventional valves and load locks because the vacuum in the analysis chamber is minimally affected by the changes in pressure in the small-volume chamber. Furthermore, in some specific embodiments of the sample plate handling system of the present teaching, inexpensive o-rings are used to provide seals between chambers of the mass spectrometer and between the outside and the chambers.

FIG. 1 illustrates a block diagram of a generic MALDI-TOF mass spectrometer system 100. The MALDI-TOF mass spectrometer system 100 includes a MALDI ion source 102 that produces and accelerates ions generated in the ion source. A sample plate on a sample plate loader 104 containing a sample of interest in a suitable matrix on the surface of the sample plate is positioned in the mass spectrometer. A laser system 106 produces pulses of light at a wavelength that is absorbed by the matrix and causes sample molecules on the sample plate to be desorbed and ionized. An ion optical system 108 focuses the ion beam produced by the ion source 102 and directs the ions toward an ion detector 111 in a time-of-flight mass analyzer 110 that separates the ions in time according to their mass to charge ratio.

The MALDI-TOF mass spectrometer system 100 includes a main chamber 112 that encloses the ion source 102, the ion optical system 108, and the time-of-flight mass spectrometer 110. A vacuum pump 114 produces and maintains a vacuum in the main chamber 112. A vacuum gauge 116 monitors the pressure in the main chamber 112. Power supplies 118 provide voltages and electrical pulses to the ion source 102, the ion optical system 108 and to the time-of-flight mass analyzer 110. The main chamber 112 also includes at least one vacuum window that allow laser pulses to propagate to the sample plate and various vacuum feedthroughs that pass electrical wires between the elements in the main chamber 112 and other elements outside the chamber (not shown).

The MALDI-TOF mass spectrometer system 100 also includes a digitizer 120 that measures and records the times between trigger pulses from the laser 106 and signals from the ion detector 111 to generate time-of-flight mass spectra. A sample plate loader 104 transmits sample plates from an external sample preparation system to the MALDI ion source 102. A computer 122 receives signals and data from the other components of the system and provides control signals to a control circuit 124 that automatically control the other components.

The MALDI-TOF mass spectrometer system 100 also includes controller 130 that transfers samples of interest to sample plate 134 by employing sample preparation system 132. Sample preparation system 132 spots samples 136 onto plates 134 along with an appropriate MALDI matrix. Sample preparation system 132 can employ either manual or robotic means. Controller 130 causes sample plate 134 to be transferred to sample plate loader 104. Controller 130 controls the sample loading and operation of the mass spectrometer either through computer 122 or by direct interaction with components such as the sample loader 104, the power supplies 118, and the laser 106. The controller 130 is responsible for "tuning" important parameters to achieve acceptable results. The controller 130 is typically a skilled person who possesses at least some detailed knowledge and expertise concerning all aspects of the system.

One aspect of the present teaching is the use of various improvements to MALDI-TOF mass spectrometer systems, which renders the system suitable for clinical applications. For example, some of these improvements are described in U.S. Pat. No. 8,735,810, entitled "Time-Of-Flight Mass Spectrometer with Ion Source and Ion Detector Electrically Connected," U.S. patent application Ser. No. 14/475,528, entitled "Method and Apparatus for Transporting Samples Plates Between Chambers of a Mass Spectrometer," and U.S. patent applicant Ser. No. 14/611,260, entitled "Method and Apparatus for Transporting Samples in a Mass Spectrometer." The entire contents of U.S. Pat. No. 8,735,810 and U.S. patent application Ser. Nos. 14/475,528 and 14/611,260 are incorporated herein by reference.

One aspect of the mass spectrometer systems of the present teaching is that the laser pulse repetition rate is in the range 1-5 kHz. Another aspect of the mass spectrometer systems of the present teaching is that the laser spot is rastered over the sample spot in order to ionize and analyze a large fraction of the sample on a sample spot. At least 10,000 laser shots are summed to obtain a spectrum, and as many as 200,000 laser shots can be employed, as necessary, to completely ionize a sample.

One feature of the ion optical system 108 for the MALDI-TOF mass spectrometer according to the present teaching is that both the sample plate 134 and the ion detector 111 output are biased at ground potential. The ion optical system 108 also provides ion focusing and control electrodes that very efficiently accelerate the ions produced by MALDI and transport these ions to the ion detector.

Another feature of the MALDI-TOF mass spectrometer system of the present teaching is that it uses a much simpler and less expensive method and apparatus for transferring sample plates from atmospheric pressure to an evacuated chamber of a mass spectrometer. In particular, one aspect of the present teaching uses manual loading of sample plates. In order to enable these simpler and less expensive methods and apparatus for transferring sample plates from atmospheric pressure to the evacuated chamber of the mass spectrometer, conventional load lock chambers and gate valves have been eliminated. The gate valves in prior art mass spectrometers are needed to seal the various chambers for separate pump down cycles. The gate valves of known mass spectrometers are complex and expensive and their use increases the processing time of the mass spectrometric analysis. Some embodiments of the sample plate handling system of the present teaching introduce new samples to be analyzed through a chamber with a volume that is much smaller than the volume of the analysis chamber. This reduces or eliminates the need for conventional valves and load locks because the vacuum in the analysis chamber is minimally affected by the changes in pressure in the small-volume chamber. Furthermore, in some specific embodiments of the sample plate handling system of the present teaching, inexpensive o-rings are used to provide seals between chambers of the mass spectrometer and between the outside and the chambers.

Figure 2:
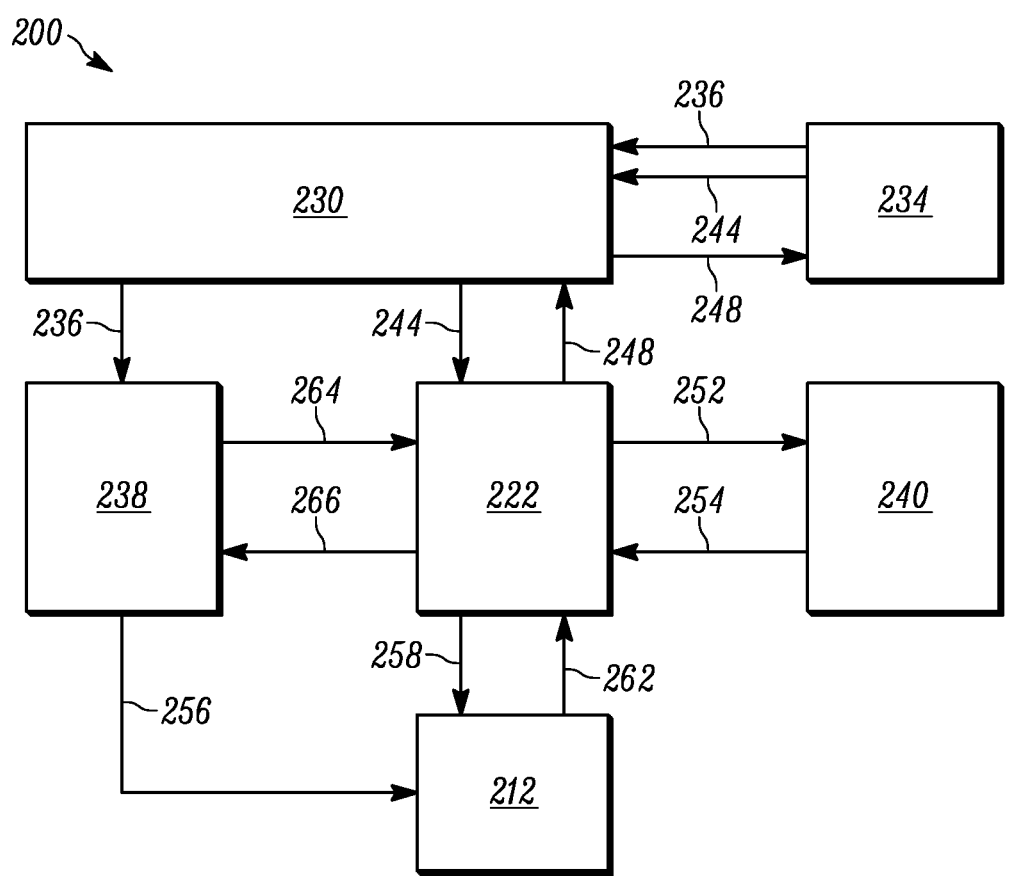
FIG. 2 illustrates a block diagram of a complete mass spectrometer system for clinical and diagnostic applications according to the present teaching.

FIG. 2 illustrates a block diagram of a complete mass spectrometer system 200 for clinical and diagnostic applications according to the present teaching. Unlike known systems, this mass spectrometer system has no direct interaction between the controller 230 and the MALDI-TOF mass spectrometer 212. Consequently, the controller 230 does not require any knowledge or expertise about mass spectrometer 212. The controller 230 can be replaced by a computer controlled robot.

The controller 230 receives sample 236 and instructions and information 244 about the sample from a clinical source 234 and then transmits the sample 236 to the sample preparation system 238 and transmits instructions and information 244 about the sample to the computer 222. The sample preparation system 238 prepares the sample for analysis by MALDI according to predetermined instructions corresponding to information 244. The sample preparation system 238 may be manual or robotic. Sample plates 256 containing samples derived from sample 236 are transferred to mass spectrometer 212. In various embodiments, the sample plates 256 are labeled by a bar code that is read by mass spectrometer 212 to correlate the sample plate with instructions 244. Database 240 is queried by computer 222 to determine the mass spectrometer settings that are required to execute instructions 244 and those settings are downloaded to mass spectrometer 212 to analyze the sample. Spectra produced by mass spectrometer 212 are digitized by computer 222 and then processed and analyzed. The results are stored and interpreted by database 240. Computer 222 prepares a report on the result 248 and transmits this to controller 230. The result can then be transmitted to the clinical source 234.

The details of the sample preparation system 238 and the mass spectrometer 212 depend on the particular application and the particular controller. In some cases, both may involve only manual operations by the controller 230. In other cases, one or both can be completely automated. Initially, the controller 230 must decide which of the mass spectrometers is appropriate for the application. The type of mass spectrometer includes linear, reflector or tandem for positive ions, negative ions, or bipolar, for a choice of either positive or negative ions. The voltages generated by the power supplies 118 (FIG. 1) can be fixed at the factory. Voltages can be programmed depending upon the particular application. Other parameters, such as laser pulse repetition rate, fluence, number of laser shots/spectrum, number of spectra/sample, and plate scanning parameters can also be set depending upon the particular application. There may also be programmed criteria for spectrum acceptance and for evaluating the quality of the spectra saved. In some methods, according to the present teaching, the mass spectrometer 212 may feedback a modified method in cases where the interpretation is uncertain or unsuccessful. The method can be derived during development and validation of an analysis, and may not be modified by the user if desired.

The combination of high resolving power and more efficient sample utilization, which are made possible by operating the MALDI TOF mass spectrometer instruments at a relatively high laser repetition rate, provides accurate intensities and masses of even very weak peaks, including those peaks due to chemical noise. Furthermore, to the extent that the noise is constant or slowly varying compared to peaks, which, for example, is the case for chromatographic effluent, the relatively high laser repetition rates make it possible to detect low-level components that would otherwise be submerged in the chemical noise background. In some methods of operation, using MALDI-TOF with high laser repetition rates according to the present teaching provide detection and quantification of samples with surface concentrations as low as a few hundred molecules per laser spot.

MALDI-TOF mass spectrometry using high laser pulse repetition rates according to the present teachings enables MALDI-TOF mass spectrometers to have wide-spread use for clinical applications. More than twenty-five years after the advent of the enabling approaches of MALDI and electrospray ionization, known instruments have only experienced limited implementations in routine clinical determinations. For example, linear MALDI-TOF instruments produced by both Bruker and BioMerieux have recently been approved by the FDA for clinical applications and pathogen identification, but these instruments operate at low laser pulse repetition rates, which are typically less than 50 Hz. These instruments also do not include many of the mass spectrometers features described herein.

Known mass spectrometer instruments produce significant noise during operation and this noise significantly limits the reproducibility of the mass spectra. One feature of the present teaching is an apparatus and methods of MALDI-TOF mass spectrometers that provide reproducible mass spectra with no significant noise. The resulting mass spectra are consistent for multiple instruments and multiple users preparing samples. The mass spectrometers of the present teaching also minimize effects due to variations in the amount and distribution of samples on the sample plate.

In addition, the mass spectrometers of the present teaching effectively reduce the variability of the results due to instrument imperfections to the point that this effect is negligible in the quality of the results obtained. Residual sources of uncontrolled variability occur during sample preparation and deposition on the sample plate, and provide variability in resolving power, as well as measured masses and intensities of the peaks in the spectrum. One feature of the mass spectrometers of the present teaching is that data variability is limited nearly exclusively by sample preparation.

The mass spectrometer features described herein allow the physical size and weight of the instrument to be much less than other known instruments. In fact, mass spectrometer instruments according to the present teaching fit comfortably on a laboratory bench and can be picked up and moved by any person of ordinary strength. In one specific embodiment, the footprint is typically less than 0.4×0.4 meters, the overall height with the linear analyzer is less than 1 meter, and the weight is less than 50 kg. In one specific embodiment, the MALDI sample plate loaded into the mass spectrometer has outside dimensions nominally 27×86 mm. This plate is designed to accommodate an active area 25×76 mm corresponding to standard microscope slides and other plates known in the art. This allows four such plates to be mounted in a standard microtiter plate format external to the instrument so that standard robotic liquid handlers can spot a set of four such plates using standard 96, 384, or 1536 formats.

One embodiment of the mass spectrometer of the present teaching includes an autoloader that sequentially transfers individual 27×86 mm plates from a set of 4 such plates mounted in a microtiter format external to the mass spectrometer. A bar code for identifying the plate may be located at any convenient location on the plate. In one embodiment, the plate is composed of a magnetic material such as 400 series stainless steel. In other embodiments, at least the outer portion of the plate is composed of magnetic material and the active area may be an insert composed of any suitable material for sample deposition, including glass and plastic. The insert must conduct electricity such that the surface does not charge significantly. One way of achieving the conductivity is to coat the plates with a very thin layer of tin oxide that is optically transparent. Plates with various levels of electrical conductivity are commercially available.

Two basic sample plate formats are now well established for many applications of mass spectrometry, as well as many other analytical instruments. These are the array format and the larger plate format, known as the microtiter format. During at least the last twenty years, systems for liquid handling and robotic manipulation of both types of plates have become ubiquitous and are available from many vendors. Many applications for MALDI-TOF mass spectrometry employ the microtiter format, but some employ the array format. The mass spectrometers of the present teaching allow the use of either format. However, one feature of the mass spectrometer of the present teaching is that it can use the smaller plate equivalent to one-quarter of the standard microtiter plate.

Also, many known mass spectrometer instruments employ a design that places the MALDI sample plate at high voltage, typically 20 kV, relative to the ground potential of the housing. Such high voltages require the use of electrical insulation that prevents breakdown conditions or corona discharge. In addition, many known mass spectrometers include flexible or moving connections between the sample plate mounted on an x-y table that can accommodate the large distances of motion that are required to scan the entire microtiter plate with the laser. Such a design requires a relatively large chamber, and is often the reason for failure when electrical discharges occur. One aspect of the mass spectrometer of the present teaching is that these large chambers are not required, thereby eliminating the associated problems.

Referring back to FIG. 1, the sample plate loader 104 according to the present teaching can be equipped with a digital camera that produces a high resolution digital image of the sample plate 134 before it transferred from the plate loader 104 to the MALDI ion source, and again as it returns to the plate loader 104 from the ion source. This reads the bar code into the computer and provides the information needed to carry out the analysis. It also provides a high resolution picture of the sample on the MALDI plate, both before and after analysis. This can be used to assess the quality of the sample preparation and deposition on the MALDI plate and can also guide the analysis by determining the most efficient way to scan the laser over the individual sample.

Figure 3:
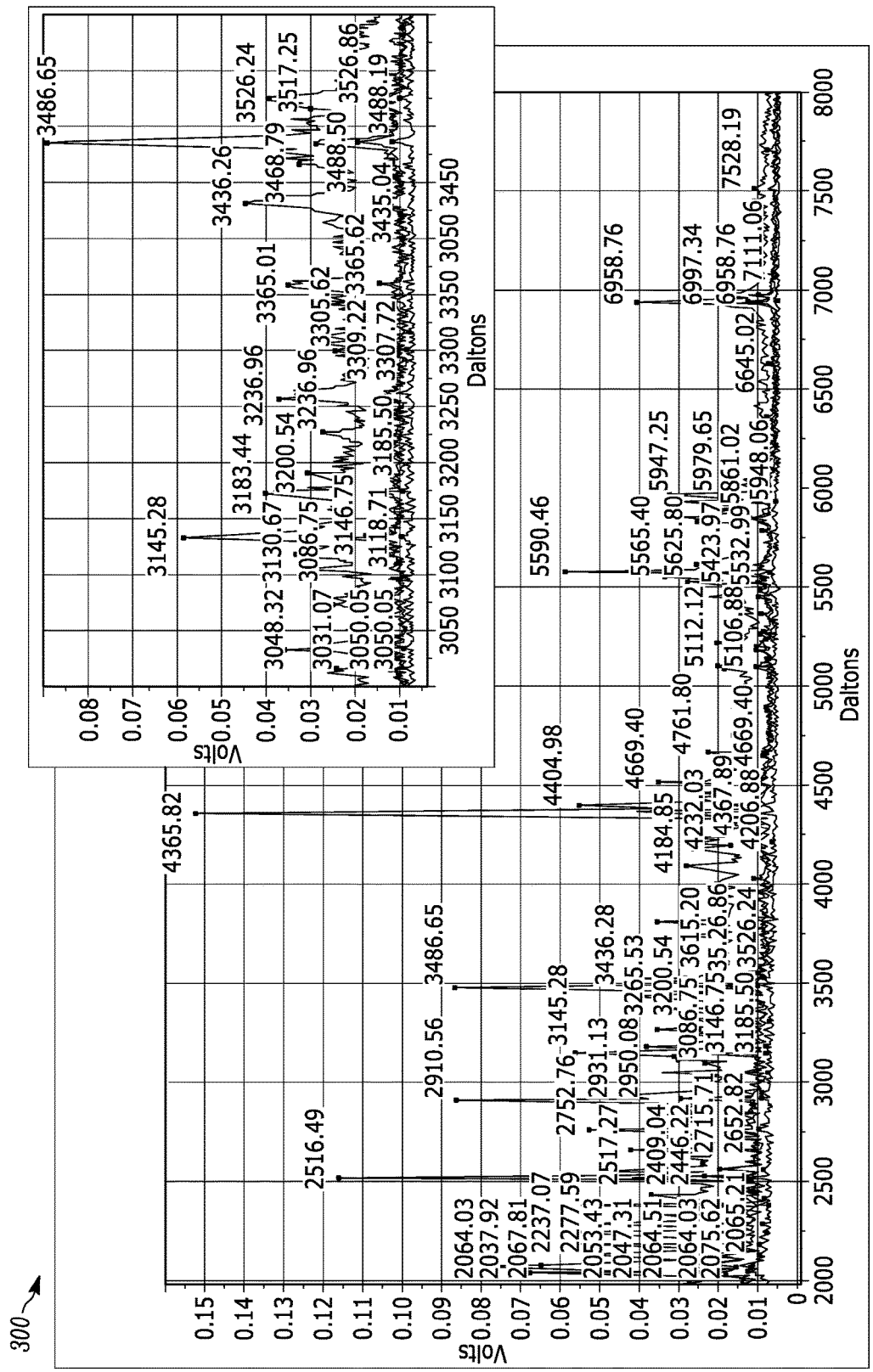
FIG. 3 illustrates spectra data taken with a known mass spectrometer of saliva spectra with fifty laser shots averaged.

Many known MALDI-TOF mass spectrometers do not produce reproducible spectra in either mass or intensity. Consequently, specialty techniques are required to utilize the resulting low quality spectra. FIG. 3 illustrates spectra data 300 taken with a known mass spectrometer of saliva spectra with fifty laser shots averaged. The data 300 shows both the intensities of the peaks and the apparent masses vary substantially amongst the various spectra.

Figure 4:
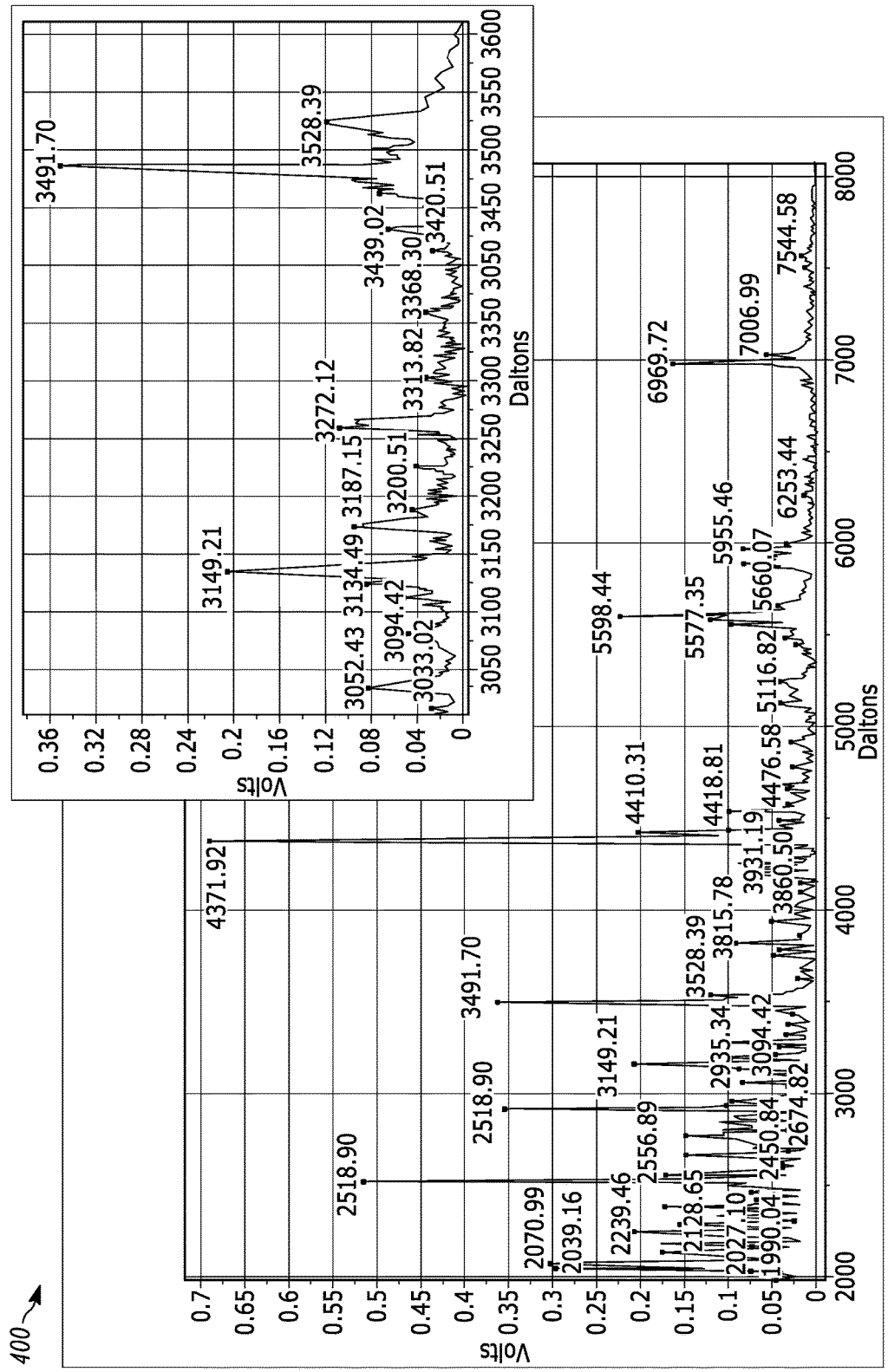
FIG. 4 illustrates spectra data obtained on the same sample spot using laser rastering according to the present teaching.

FIG. 4 illustrates spectral data 400 obtained on the same sample spot using laser rastering according to the present teaching. The laser beam is rastered over a sample spot of saliva. For this particular data 400, 11,900 light pulses are averaged to generate the spectra. The spectral data 400 shows that the resulting peaks of the saliva spectrum are well resolved. Furthermore, the resulting saliva spectrum has low noise as illustrated by the smoothness of the spectrum curve.

Figure 5:
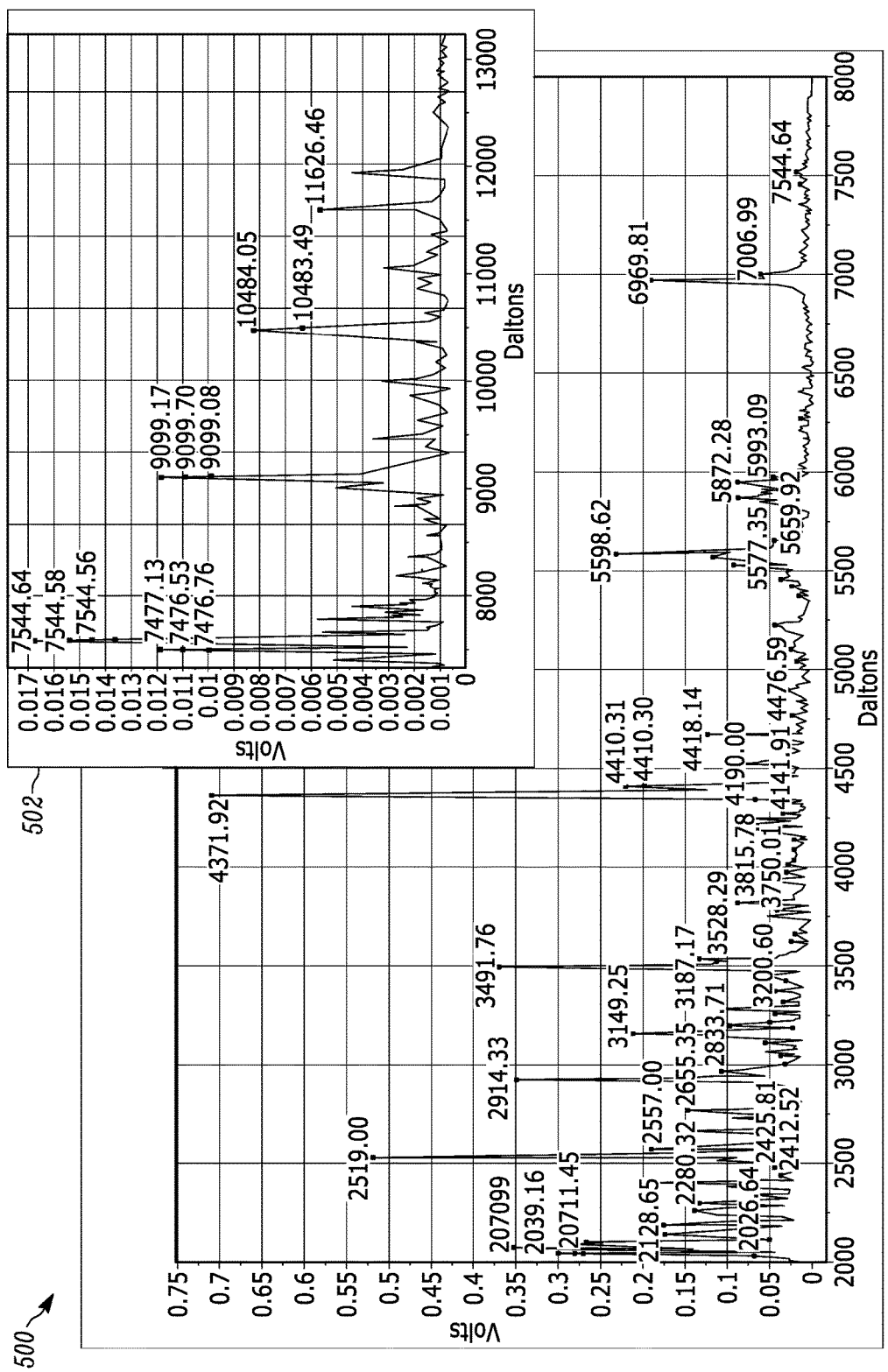
FIG. 5 illustrates data from a MALDI-TOF mass spectrometer saliva spectrum from four distinct sample spots using the laser rastering with 11,900 light pulses averaged according to the present teaching.

FIG. 5 illustrates spectra data 500 from a MALDI-TOF mass spectrometer saliva spectrum from four distinct sample spots using the laser rastering with 11,000 laser pulses averaged according to the present teaching. FIG. 5 also shows an expanded region 502 of the spectra 500. The data illustrated in FIG. 5 show that both the intensity and apparent mass of the peaks show almost no detected variation across four distinct sample spots using the MALDI-TOF mass spectrometer laser rastering and averaging of the present teaching. Thus, one important feature of the present teaching is that spectra obtained from distinct sample spots are reproducible.

Figure 6A:
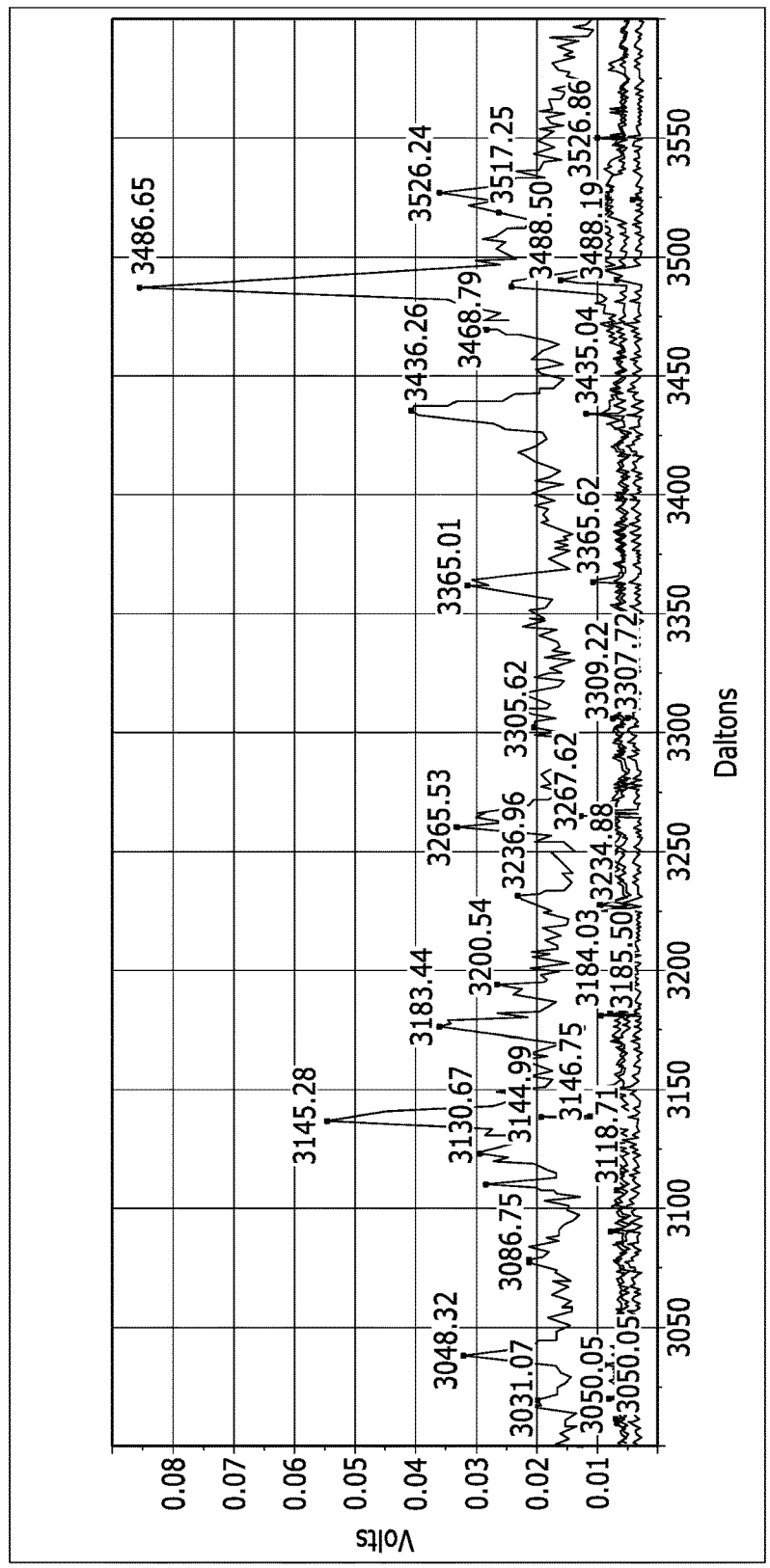
FIG. 6A illustrates data from four prior art saliva spectra with fifty laser pulses averaged.
Figure 6B:
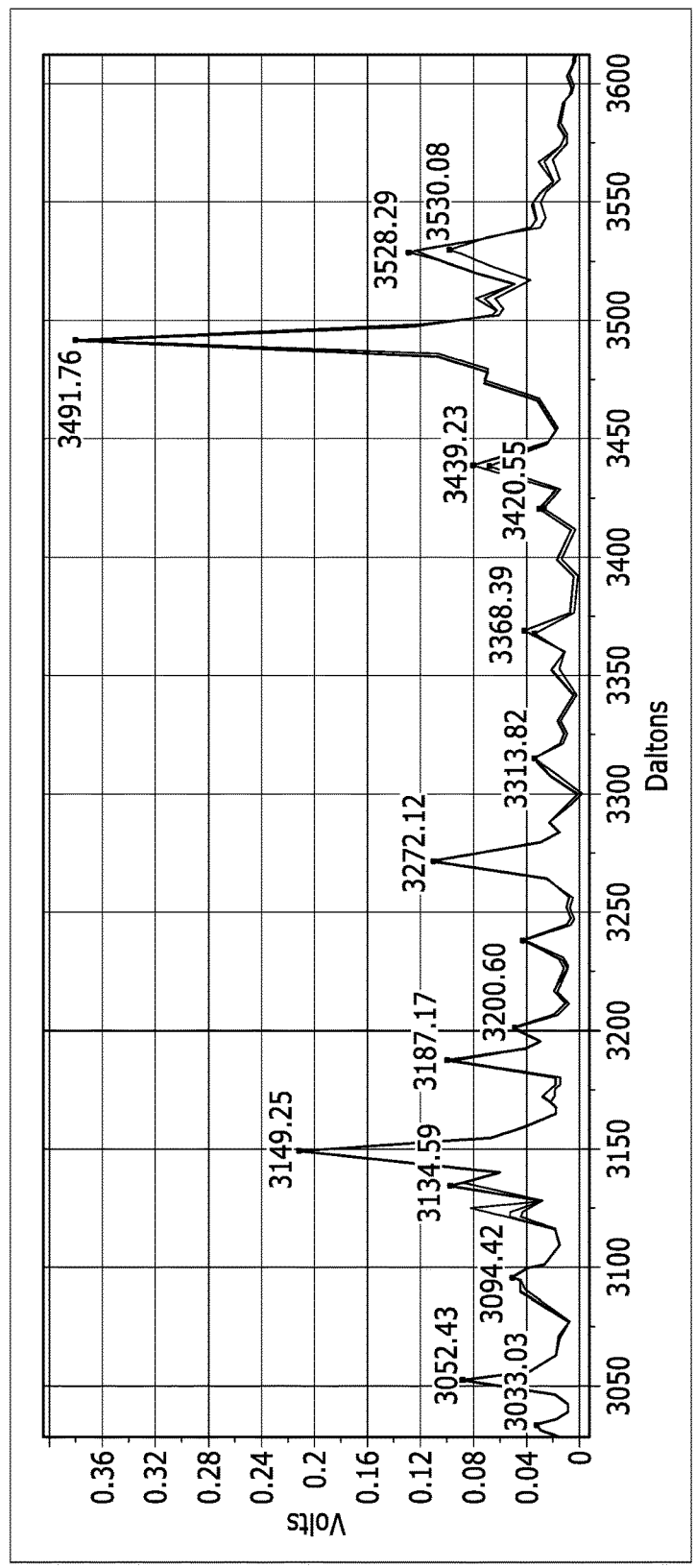
FIG. 6B illustrates data from four MALDI-TOF mass spectrometer saliva spectra with 11,000 laser pulses over mass range 3 to 3.6 kDa.

FIG. 6A illustrates data from four prior art saliva spectra with fifty laser pulses averaged. FIG. 6B illustrates data from four MALDI-TOF mass spectrometer saliva spectra with 11,000 laser pulses over mass range 3 to 3.6 kDa. The comparison of data in FIGS. 6A and 6B shows significant improvement in reproducibility using the methods of the present teaching compared with the prior art. For example, prior art saliva spectra with 50 laser pulses show multiple peaks at 3486.65, 3488.5 and 3488.19. Saliva spectra obtained using the apparatus and method of the present teaching shows all four spectra exhibits substantially a single peak at 3491.76.

Thus, one method of mass spectrometry according to the present teaching is to first perform MALDI-TOF mass spectrometry to obtain a mass spectrum and then to perform peak detection on the mass spectra to determine if a predetermined intensity is exceeded. Many techniques for peak detection are known in the art. One aspect of the present teaching is that it has been determined that the "wavelet method" of peak detection works particularly well with the complex spectra produced using MALDI-TOF mass spectrometry. See, for example, Du P, Kibbe W A and Lin S M, Peak Detection of Mass Spectrometry Spectrum by Continuous Wavelet Transform based Pattern Matching, (2006) Bioinformatics, 22, 2059-2065. It has been found that this method accurately determines peak centroids, even when peaks are only partially resolved. It has also been found that this method reliably produces a realistic determination of the signal-to-noise ratio for each peak detected. If the signal-to-noise ratio is determined by ion statistics, then the signal-to-noise ratio is equal to the square root of the number of ions in the peak.

In order to directly determine the number of ions in a spectral peak, accurate calibration of the detector gain is required. This is often difficult to accomplish. However, using the wavelet method according to the present teaching, the signal-to-noise ratio (S/N) can be determined directly from the measured spectrum and does not depend on gain of the detector or normalization of the spectra. Thus, using the wavelet method according to the present teaching, the square of signal-to-noise ratio is used as the best measure of intensity of a peak in the spectrum. For example, with a signal-to-noise ratio equal to three, the probability that the peak is statistically different from the noise is about 95%. Therefore, if we accept only peaks with signal-to-noise ratios greater than three, we can be confident that noise on the spectrum is not significantly represented as peaks. In a complex spectrum covering the mass range of 2 kDa to 20 kDa, the number of peaks detected with a signal-to-noise greater than three is often less than 200 peaks. Thus, by peak detection, we have reduced the size of the array from about 50,000 peaks or more to 200 or less peaks.

Thus, MALDI-TOF mass spectrometers according to the present teaching are designed for routine clinical applications, and are fully automated, and require little or no expertise in mass spectrometry. Controllers simply prepare the samples according to a protocol established for the application, and then load the sample plates into the instrument for analysis. The instrument parameters are determined from data provided with the samples. Data acquisition, processing to interpret the data, and database searching can be fully automated. No other interaction between the controller and the instrument is required.

Equivalents

While the Applicant's teaching is described in conjunction with various embodiments, it is not intended that the Applicant's teaching be limited to such embodiments.

On the contrary, the Applicant's teaching encompass various alternatives, modifications, and equivalents, as will be appreciated by those of skill in the art, which may be made therein without departing from the spirit and scope of the teaching.

We claim:

1. A mass spectrometer system for analysis of clinical samples, the mass spectrometer system comprising:
   a) a source of clinical samples;
   b) a controller that receives the clinical samples from the source of clinical samples;
   c) a sample preparation system that receives the clinical samples from the controller and that processes the clinical samples to produce an extract suitable for analysis by MALDI-TOF mass spectrometry and that deposits the extract on a sample plate together with a MALDI matrix;
   d) a sample plate loading mechanism that transports sample plates from the sample preparation system into an evacuated ion source through a small-volume chamber comprising a volume that is smaller than a volume of the evacuated ion source such that a vacuum in the evacuated ion source is minimally affected by a change in pressure in the small-volume chamber;
   e) a MALDI-TOF mass spectrometer that ionizes and analyzes samples on the sample plate and that generates a mass spectrum of components in the clinical samples; and
   f) a computer system that receives data from the MALDI-TOF mass spectrometer and that processes and interprets the received data to generate a mass spectrum.

2. The mass spectrometer system of claim 1 wherein the controller comprises a computer controlled robot.

3. The mass spectrometer system of claim 1 wherein the controller sends information about the clinical samples to the MALDI-TOF mass spectrometer.

4. The mass spectrometer system of claim 1 wherein the controller changes parameters in the MALDI-TOF mass spectrometer based on the generated mass spectrum.

5. The mass spectrometer system of claim 1 wherein the sample preparation system comprises a robotic mechanism.

6. The mass spectrometer system of claim 1 wherein the sample plate loading mechanism comprises a manual sample plate loading mechanism.

7. The mass spectrometer system of claim 1 wherein the controller receives information about the clinical samples from the source of the clinical samples.

8. The mass spectrometer system of claim 1 wherein the computer system provides analytical results on the mass spectrum of components of the clinical sample.

9. The mass spectrometer system of claim 1 wherein the sample plate and an ion detector in the MALDI-TOF mass spectrometer are biased at ground potential.

10. The mass spectrometer system of claim 1 wherein there is no direct interaction between the controller and the MALDI-TOF mass spectrometer.

11. The mass spectrometer system of claim 1 wherein the sample plate is labeled with a bar code.

12. The mass spectrometer system of claim 11 wherein the MALDI-TOF mass spectrometer comprises a bar code reader and processor that correlate the sample plate with associated instructions.

13. The mass spectrometer system of claim 1 wherein the MALDI-TOF mass spectrometer comprises a linear mass spectrometer.

14. The mass spectrometer system of claim 1 wherein the MALDI-TOF mass spectrometer comprises a tandem mass spectrometer.

15. The mass spectrometer system of claim 1 wherein the MALDI-TOF mass spectrometer comprises a reflector mass spectrometer.

16. The mass spectrometer system of claim 1 wherein the sample plate loading mechanism comprises an autoloader.

17. The mass spectrometer system of claim 1 wherein the sample plate loading mechanism is configured for a microtiter format.

18. The mass spectrometer system of claim 1 wherein the sample plate loading mechanism is configured for an array format.

19. A method of analyzing clinical samples with a MALDI-TOF mass spectrometer, the method comprising:
   a) providing clinical samples;
   b) preparing the clinical samples for MALDI-TOF mass spectrometry by depositing an extract of the clinical samples on a sample plate together with a MALDI matrix;
   c) loading the sample plate into an evacuated ion source chamber of the MALDI-TOF mass spectrometer using a small-volume chamber comprising a volume that is smaller than a volume of the evacuated ion source such that a vacuum in the evacuated ion source is minimally affected by a change in pressure in the small-volume chamber;

d) ionizing the extract of the clinical samples and MALDI matrix on the sample plate;

e) performing time-of-flight mass spectrometry of the ionized extract of the clinical samples and MALDI matrix and generating a mass spectrum of components in the clinical samples;

f) performing peak detection on the mass spectrum using a wavelet method to determine if a predetermined intensity is exceeded; and g) interpreting the generated mass spectrum.

20. The method of claim 19 wherein the ionizing comprises rastering a laser beam over a sample spot a plurality of times in order to ionize a large fraction of the clinical sample on a sample spot.

21. The method of claim 19 wherein the ionizing the extract of the clinical samples comprises pulsing a laser a plurality of times on an area of the clinical sample.

22. The method of claim 19 wherein the ionizing the clinical samples comprises pulsing a laser a plurality of times so that a portion of the clinical sample is completely ionized.

23. The method of claim 22 wherein a number of the plurality of times that the laser is pulsed is greater than 10,000.

24. The method of claim 19 wherein the ionizing the extract of the clinical samples on the sample plate comprises ionizing positive ions.

25. The method of claim 19 wherein the ionizing the extract of the clinical samples on the sample plate comprises ionizing negative ions.

26. The method of claim 19 wherein a number of the plurality of times that the laser is pulsed is chosen to reduce noise in the mass spectrum.

* * * * *